United States Patent
Parker, Jr. et al.

(10) Patent No.: US 10,025,907 B1
(45) Date of Patent: Jul. 17, 2018

(54) PHARMACEUTICAL PRESCRIPTION TRANSFER SYSTEM

(71) Applicant: Fast Rx Transfer, LLC, Sugar Land, TX (US)

(72) Inventors: William Parker, Jr., Pearland, TX (US); Marcus Davis, Pearland, TX (US)

(73) Assignee: Fast Rx Transfer, LLC, Sugar Land, TX (US)

( * ) Notice: Subject to any disclaimer, the term of this patent is extended or adjusted under 35 U.S.C. 154(b) by 0 days.

(21) Appl. No.: 15/803,216

(22) Filed: Nov. 3, 2017

(51) Int. Cl.
| | |
|---|---|
| G06F 17/00 | (2006.01) |
| G06F 19/00 | (2018.01) |
| G16H 80/00 | (2018.01) |
| G16H 10/60 | (2018.01) |
| G06Q 50/22 | (2018.01) |
| G06Q 30/02 | (2012.01) |
| G06Q 50/24 | (2012.01) |

(52) U.S. Cl.
CPC ......... *G06F 19/3456* (2013.01); *G06Q 50/22* (2013.01); *G16H 10/60* (2018.01); *G16H 80/00* (2018.01); *G06Q 30/0283* (2013.01); *G06Q 50/24* (2013.01)

(58) Field of Classification Search
CPC ............... G06F 19/3456; G06F 19/322; G06F 19/3425; G06Q 10/00; G06Q 50/22; G06Q 50/24; G06Q 30/0283; G16H 80/00
USPC .......................................................... 235/375
See application file for complete search history.

(56) References Cited

U.S. PATENT DOCUMENTS

| | | | | |
|---|---|---|---|---|
| 5,974,124 A | * | 10/1999 | Schlueter, Jr. | ....... A61B 5/0002 379/106.02 |
| 7,769,601 B1 | * | 8/2010 | Bleser | ................. G06F 19/326 705/26.8 |
| 8,626,530 B1 | * | 1/2014 | Tran | ...................... G06Q 50/22 705/2 |
| 2004/0172295 A1 | * | 9/2004 | Dahlin | ............... G06F 19/3456 705/2 |
| 2008/0073432 A1 | * | 3/2008 | Barenburg | ............ G06Q 10/08 235/385 |
| 2008/0126135 A1 | * | 5/2008 | Woo | .................... G06F 19/3456 705/3 |
| 2008/0215359 A1 | * | 9/2008 | Liccardo | ............ G06F 19/3456 705/2 |
| 2009/0112628 A1 | * | 4/2009 | Claud, III | .......... G06F 19/3425 705/3 |

(Continued)

*Primary Examiner* — Claude J Brown
(74) *Attorney, Agent, or Firm* — Maier & Maier, PLLC (57) ABSTRACT

A pharmaceutical prescription transfer system making use of a transferring pharmacy module and a receiving pharmacy module, each of which may be made available to pharmacies through a super administrator portal used for management. Such a system may allow pharmacies to rapidly transfer patient prescriptions electronically and may facilitate simple billing of transferring pharmacies upon transfer and receiving pharmacies upon successful and approved receipt. Such a system may be integrated with third-party applications, such as payment processing software, an electronic fax system, a drug database used for validation, and a pharmacy management application, which may automatically update or be automatically updated by the transfer system when drugs are dispensed or at other times.

18 Claims, 4 Drawing Sheets

(56) References Cited

U.S. PATENT DOCUMENTS

| | | | |
|---|---|---|---|
| 2011/0288883 A1* | 11/2011 | Knoth | G06Q 10/087 705/3 |
| 2011/0307265 A1* | 12/2011 | Bannis | G06Q 50/22 705/2 |
| 2012/0253830 A1* | 10/2012 | John | G06Q 30/00 705/2 |
| 2013/0173287 A1* | 7/2013 | Cashman | E04H 3/08 705/2 |
| 2015/0161351 A1* | 6/2015 | Scalpati | G06F 19/3456 705/2 |
| 2016/0103978 A1* | 4/2016 | Stong | G06F 19/3481 705/3 |
| 2016/0232296 A1* | 8/2016 | Cohen | G06Q 50/22 |
| 2016/0371460 A1* | 12/2016 | Minemura | G06Q 50/22 |
| 2017/0076058 A1* | 3/2017 | Stong | G06F 19/3456 |

\* cited by examiner

Transfer Complete Details

| Requesting Pharmacy Name | Responding Pharmacy Name |
|---|---|
| Marcus Pharmacy | Kasco Pharmacy |
| Requesting Pharmacy Adddress | Responding Pharmacy Adddress |
| 1232 State St | 10369 West Mike St. |
| Requesting Pharmacy DEA | Responding Pharmacy DEA |
| FM123456789 | AK47412586 |
| Requesting Pharmacist Name | Responding Pharmacist Name |
| Marcus Davis | Marcus Davis |

← 402
← 404
406

Requesting Pharmacy Comment

Patient Name*
Jane Doe

Patient Date of Birth*
10/30/2017

Patient Address
Home Address

Prescription Drug Name*
Aspirin 325 MG Oral Tablet [Ascriptin]

Prescription Number*
111222333

Prescription Drug Quantity*
30

Directions*
TAKE 1 TABLET BY MOUTH DAILY

Original Date Written*
11/01/2017

Date Last Filled*
11/01/2017

Refills Remaining*
4

Provider Name*
Dr. John Doe

Provider Phone Number*
8885551111

Provider NPI
Provider NPI

Provider DEA
Provider DEA

Comments
Comments

Fig. 4

PHARMACEUTICAL PRESCRIPTION TRANSFER SYSTEM

BACKGROUND

Nearly half of Americans take at least one prescription drug, for matters ranging from chronic health problems to seasonal allergies. However, in recent years, the prices of prescription drugs have risen massively, to the point where, according to one study conducted by the AARP, the average cost of a year's supply of prescription drugs has doubled from 2006 to 2013, from approximately $5,500 to over $11,000. These prices are already unaffordable for much of the country (such as retired persons), and are predicted to continue to rise dramatically.

There are numerous reasons for these increases. For example, in many cases, large price increases can arise from a shortage or a change in insurance coverage. Manufacturers may also raise prices because there are a lack of generics or other competitors in the market.

Increasingly, customers have begun making it a priority to save as much money as they can on prescription drugs. For example, many customers have resorted to purchasing prescription drugs online from Canada, which generally enjoys much cheaper prices. While this is technically illegal (under the Prescription Drug Marketing Act of 1987, it is illegal for anyone other than the original manufacturer to bring prescription drugs into the country, though the law appears to be rarely enforced by U.S. officials) and often unsafe (a large number of medications ordered online turn out to be counterfeit, or are at the very least sourced from a different country other than Canada), it remains a somewhat common practice.

Those customers interested in staying on the right side of the law can, theoretically, still get a significant amount of benefit from comparison shopping. One study conducted by Consumer Reports found that costs can vary as much as 10 times from one retailer to another, with the least expensive retailers tending to be non-chain drugstores (such as "mom-and-pop" operations). Numerous apps and websites like GOODRX and LOWEST MED have sprung up in order to try to offer customers a better deal when initially seeking to fill a prescription; these programs provide customers with the prices of medications at various pharmacies in their local area, as well as the prices of comparable generic drugs or competitor drugs, which allow customers to fill the prescription at the pharmacy offering the lowest price.

However, these apps and websites offer significantly less benefit to a customer that has a prescription with one pharmacy and wants to transfer to another. While many chain drugstores try to make it as easy as possible for a customer to transfer their prescription to the chain drugstore (for example, many have staff that will call the pharmacy holding the prescription and the prescribing physician and make necessary arrangements) it can still be a lengthy and complicated process that will often require the customer to wait up to a week to have their prescription transferred. Further, the pharmacies that typically offer the best deals to customers (the aforementioned "mom-and-pop" stores) generally are the least likely to offer transfer services to customers, requiring the customers to jump through additional hoops in order to transfer their prescription.

SUMMARY

A pharmaceutical prescription transfer system may be disclosed, which may allow pharmacies to rapidly transfer patient prescriptions electronically. In some exemplary embodiments, such a system may be implemented via a software portal, in such a manner as to allow a fee to be charged based on each electronic transaction or based on other usage of the portal such as may be desired. In an exemplary embodiment, a transfer system may be scalable so as to be accessible to both independent pharmacies and large chain pharmacies, and may, for example, permit independent pharmacies to participate through their current dispensing software vendor, while large chain pharmacies can participate directly with the pharmaceutical prescription transfer system.

According to an exemplary embodiment, a pharmaceutical prescription transfer system may include a directory of pharmacies which may include and may be searchable by the pharmacy name, the pharmacy address, city, and state, the pharmacy NCPDP number, the pharmacy phone number, or any other relevant information. To make use of the pharmaceutical prescription transfer system, a user may first select a pharmacy from this directory after performing any necessary searching of the system. Once the user has selected a pharmacy, the user may be provided with the option to enter prescription transfer information.

According to an exemplary embodiment, the pharmaceutical prescription transfer system may request prescription transfer information including, for example, the patient name, the patient prescription number, the patient date of birth, the drug name, and any other fields that may be desired. In some exemplary embodiments, some of this information (such as, for example, patient name and prescription number) may be mandatory and some of this information (such as, for example, date of birth) may be optional or may be retrievable from other patient records based on a name and prescription number (or other information) being added.

Once a prescription transfer request has been crafted within the pharmaceutical prescription transfer system, it may be sent to the transferring pharmacy via the pharmaceutical prescription transfer system. Once sent, the transferring pharmacy may receive a notification within the pharmaceutical prescription transfer system software that may provide all transfer information that had been provided to the pharmaceutical prescription transfer system or which may be retrievable by the pharmaceutical prescription transfer system based on the information provided.

Once the transferring pharmacy receives the notification, it may then select the prescription or prescriptions to be transferred and may then submit this information to the pharmaceutical prescription transfer system. Alternatively, according to an exemplary embodiment, the pharmaceutical prescription transfer system may offer an option to print the transfer information in order to allow the transferring pharmacy to fill out the transfer request by hand; the pharmaceutical prescription transfer system may then offer an internal scanned document transfer system (such as an electronic fax system) or, alternatively, the transferring pharmacy may send the transfer by an external fax (or other method) and a user of the pharmaceutical prescription transfer system may have an option to select that the transfer was done by fax.

Once the transferring pharmacy has provided this information (or has selected that the transfer will be done by an external method, such as by an external fax), the pharmaceutical prescription transfer system may provide a notification to the receiving pharmacy via the pharmaceutical prescription transfer system or otherwise indicating that the transfer has been completed by the transferring pharmacy.

This may be, for example, a "done" notification, provided along with the transferred prescription information, or may be a notification that the material has been faxed or sent by another method (such as, for example, an e-fax), such as may be desired.

According to an exemplary embodiment, a pharmaceutical prescription transfer system, including a transferring pharmacy module and a receiving pharmacy module, each of the transferring pharmacy module and the receiving pharmacy module including a processor, a memory, and a network connection, may be disclosed. The transferring pharmacy module may be configured to perform the steps of: accessing, with the processor, from a list of patients, a patient record, and retrieving patient information from the patient record; populating, with the processor, a transfer request form with the patient information; sending, to the receiving pharmacy module, the transfer request form including a transferred prescription, and a transfer notification; maintaining a transferred prescription status record for the transferred prescription; receiving, via the network connection, a receipt notification from the receiving pharmacy module; and providing the receipt notification to a transferring module user; the receiving pharmacy module being configured to perform the steps of receiving, via a network connection, a transfer request notification from the transferring pharmacy module, the transfer request notification including the patient information; providing the transfer notification to a receiving module user; updating the transferred prescription status record to a received status and providing the receipt notification to the transferring pharmacy module; and authorizing dispensation of the transferred prescription.

BRIEF DESCRIPTION OF THE FIGURES

Advantages of embodiments of the present invention will be apparent from the following detailed description of the exemplary embodiments thereof, which description should be considered in conjunction with the accompanying drawings in which like numerals indicate like elements, in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequences of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

According to an exemplary embodiment, and referring generally to the Figures, various exemplary implementations of a pharmaceutical prescription transfer system may be disclosed.

Figure 1:
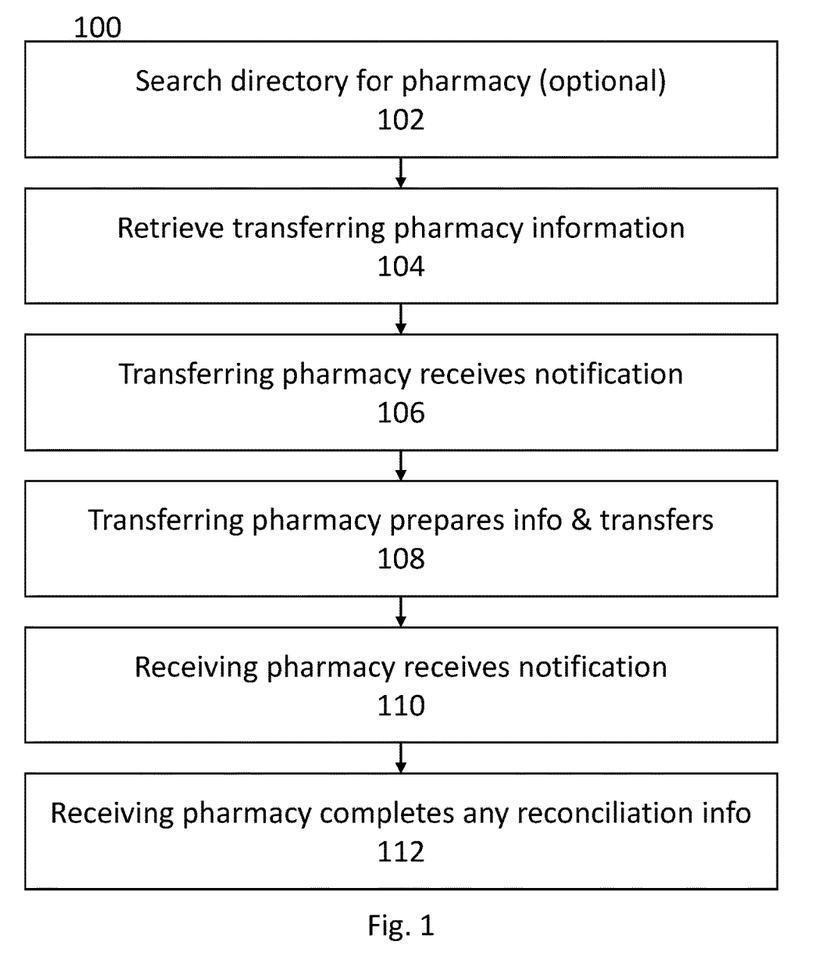
FIG. 1 is an exemplary embodiment of a process for using a pharmaceutical prescription transfer system.

Turning now to exemplary FIG. 1, FIG. 1 displays an exemplary embodiment of a process for using a pharmaceutical prescription transfer system 100. Such a process may allow pharmacies to rapidly transfer patient prescriptions electronically. In some exemplary embodiments, such a process may be performed via a software portal, in such a manner as to allow a fee to be charged based on each electronic transaction or based on other usage of the portal such as may be desired. For example, each execution of a partial stage of the process by each of the transferring pharmacy and/or the receiving pharmacy may result in a small fee being charged to the transferring pharmacy and/or the receiving pharmacy, or to one or the other (such as just the receiving pharmacy).

According to an exemplary embodiment, a pharmaceutical prescription transfer system may include a directory of pharmacies which may include and may be searchable by the pharmacy name, the pharmacy address, city, and state, the pharmacy NCPDP number, the pharmacy phone number, or any other relevant information. To make use of the pharmaceutical prescription transfer system, a user may first search this directory 102, if desired, or may otherwise locate a pharmacy in the directory. The user may then select a pharmacy from this directory, which may cause the pharmaceutical prescription transfer system to receive necessary data about the transferring pharmacy 104. The user may then be provided with the option to enter prescription transfer information to send to the transferring pharmacy as part of a transfer request.

According to an exemplary embodiment, the pharmaceutical prescription transfer system may request prescription transfer information including, for example, the patient name, the patient prescription number, the patient date of birth, the drug name, and any other fields that may be desired. In some exemplary embodiments, some of this information (such as, for example, patient name and prescription number) may be mandatory and some of this information (such as, for example, date of birth) may be optional or may be retrievable from other patient records based on a name and prescription number (or other information) being added.

Once a prescription transfer request has been crafted within the pharmaceutical prescription transfer system, it may be sent to the transferring pharmacy via the pharmaceutical prescription transfer system. Once sent, the transferring pharmacy may receive a notification 106 within the pharmaceutical prescription transfer system software. In an exemplary embodiment, this notification may provide all transfer information that had been provided to the pharmaceutical prescription transfer system; alternatively, this information may be retrievable by the pharmaceutical prescription transfer system based on the information provided.

Once the transferring pharmacy receives the notification 106, it may then select the prescription or prescriptions to be transferred and may then submit this information to the pharmaceutical prescription transfer system 108. Alternatively, according to an exemplary embodiment, the pharmaceutical prescription transfer system may offer an option to print the transfer information in order to allow the transferring pharmacy to fill out the transfer request by hand, or otherwise by the use of an external system. In some exemplary embodiments, for such documents, the pharmaceutical prescription transfer system may provide an internal scanned document transfer system (such as an electronic fax system) by which the transferring pharmacy can scan and fax the transfer request document through the pharmaceutical prescription transfer system. Alternatively, the transferring pharmacy may send the transfer by an external fax 108 (or other method) and may then indicate, via the pharmaceutical prescription transfer system, that the transfer has been made by this external system. (This may include, for example, selecting a box with the option "sent by fax.")

Once the transferring pharmacy has provided the necessary prescription information 108 (or has selected that the transfer will be or has been done by an external method, such as by an external fax), the pharmaceutical prescription transfer system may provide a notification to the receiving pharmacy 110 via the pharmaceutical prescription transfer system (or by some other method, such as via an automated text message or email) indicating that the transfer has been completed by the transferring pharmacy. This may be, for example, a "done" notification, provided along with the transferred prescription information, or may be a notification that the material has been faxed or sent by another method (such as, for example, an e-fax), such as may be desired. If it is necessary to complete any further reconciliation information, this may then be performed by the receiving pharmacy 112. Such a system may allow a prescription transfer to function in near-real-time, for example while a customer is in the receiving pharmacy, and may allow the collection and integration of pharmaceutical transfer data with other pharmaceutical record-keeping systems.

Figure 2:
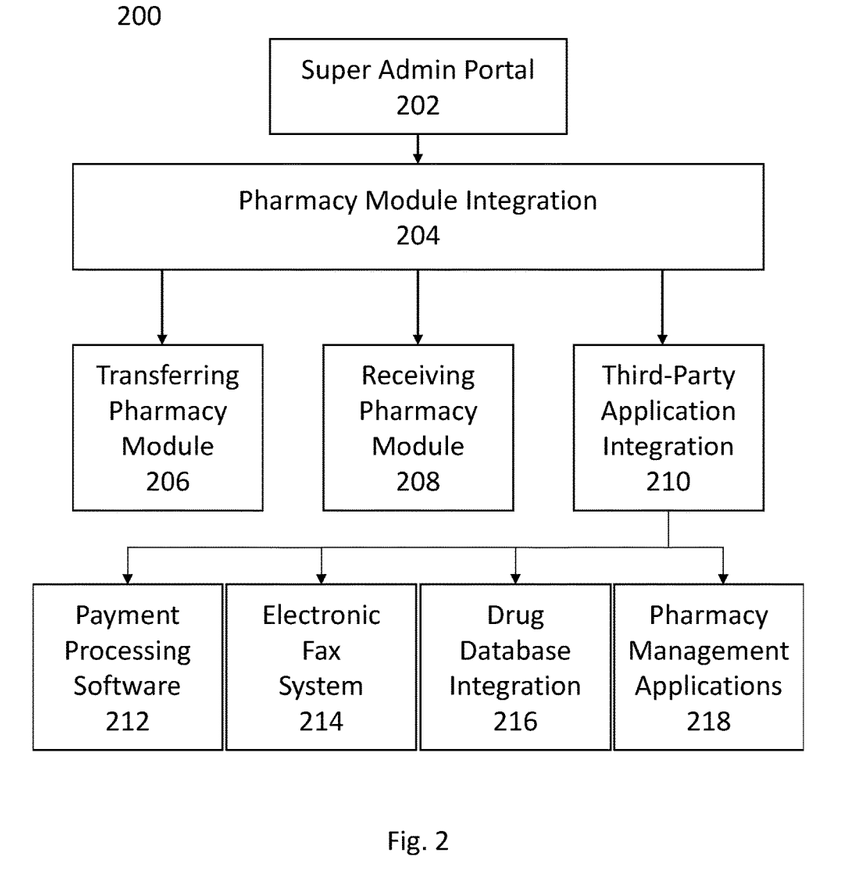
FIG. 2 is an exemplary embodiment of a pharmaceutical prescription transfer system architecture.

Turning now to exemplary FIG. 2, FIG. 2 may show an exemplary embodiment of a pharmaceutical prescription transfer system architecture 200. According to an exemplary embodiment, a pharmaceutical prescription transfer system 200 may include a super admin portal 202, one or more integrated modules 204 such as a transferring pharmacy module 206, a receiving pharmacy module 208, and third-party applications 210 integrated into the pharmaceutical prescription transfer system 200. Such third-party applications 210 may include, for example, payment processing software 212, an electronic fax system or other scanned document transfer system 214, a drug database integration system 216, and integration with a pharmacy management application 218. Other third-party applications 210 may be integrated with a pharmaceutical prescription transfer system 200, as may be desired.

Looking first at the super admin portal 202, the super admin portal 202 may allow one or more administrators of the pharmaceutical prescription transfer system 200 system to make certain adjustments or alterations to the pharmaceutical prescription transfer system 200 that may be forbidden to pharmacy-level administrators. For example, according to an exemplary embodiment, a super administrator can, through the super admin portal 202 and upon providing credentials, register a pharmacy for use in the pharmaceutical prescription transfer system 200, which may require, for example, a pharmacy name, a pharmacy national provider identifier (NPI), a pharmacy address, pharmacy contact information, pharmacy billing information, and any other information such as may be desired.

According to an exemplary embodiment, a super administrator may further be able to, through a super admin portal 202, add locations of the pharmacy, either automatically or manually, or may be able to authorize a lower-level administrator (such as a pharmacy-level administrator) or other party to perform this function (or any other functions such as may be desired). According to an exemplary embodiment, a super administrator may be able to manually provide this information by manually entering the location data and selecting an option to add a new location. According to another exemplary embodiment, a super administrator may be able to automatically provide this information by accessing a location list or repository for the pharmacy, which may include, for example, uploading a file (such as a .csv file in a pre-defined format) with the location information.

According to an exemplary embodiment, pharmacy billing information may include, for example, credit card or ACH information. However, other methods of billing may also be understood; for example, it may alternatively be desired (for one or more pharmacy clients) that the pharmacy receive a written invoice and provide payment accordingly. In such exemplary embodiments, an invoice may be sent to the pharmacy client, permitting the client to pay by check or an alternative payment method. Other payment methods, such as electronic payment systems or cryptocurrency systems, may also be integrated with the system as may be desired, and may be provided through internal software or through external payment processing software 212.

According to an exemplary embodiment, a super administrator may further be able to, through a super admin portal 202, view or manage the entire list of pharmacies that have been integrated with the system. For example, according to some exemplary embodiments, details like miscellaneous pharmacy details, pharmacy membership history or membership status such as an active or inactive status, and so forth may be viewable or editable by a super administrator. For example, in addition to viewing a membership status, a super administrator may be able to change a membership status, for example activating or deactivating a pharmacy such as may be desired.

According to an exemplary embodiment, a super administrator may further be able to, through a super admin portal 202, add, remove, deactivate, activate or edit the main client admin user or users (or any client admin user or users) for a particular pharmacy. As previously discussed, a super administrator may further be able to determine what privileges to provide to each client admin user; for example, for a large pharmacy franchise, it may be desirable to provide a corporate representative acting as main client admin user with the ability to add other admin users (franchisees) for that client, while for a small pharmacy this may not be a necessary permission.

According to an exemplary embodiment, a super administrator may further be able to, through a super admin portal 202, generate reporting information for the portal. For example, according to an exemplary embodiment, the super administrator may be able to generate reports including information on the number of transactions in a particular selection (for example, among all pharmacies, among particular pharmacies, among pharmacies in a certain area, inside a certain date range, and so forth), revenue from a particular pharmacy or set of pharmacies (which again may be filterable by similar criteria; other reports may likewise be filterable), pharmacy response rates (for example, requested transferring pharmacies or requested receiving pharmacies that did not respond to notifications, or response times for responding to notifications), and summary reports (such as, for example, an "end of day transaction detail" report).

According to an exemplary embodiment, individual pharmacies may have administrators able to add, edit, or remove their own information at the pharmacy level, which may be called "client administrators" or "client admins." According to an exemplary embodiment, a Pharmacy may be able to self-register itself through the portal by entering certain requested information, like pharmacy name, NPI, address, contact information, and billing information. (In an exemplary embodiment, default billing information may be based on a credit card or other payment method that may be provided, captured and validated during registration; in an exemplary embodiment, this may be paired with a third-party payment gateway integration system 212.)

According to an exemplary embodiment, once registered, the pharmacy will get a Client Admin user account; in an exemplary embodiment, the pharmacy may be asked to enter username and/or password details during a registration stage as well as the other information provided above. In another exemplary embodiment, the first time a user accesses the portal, he/she will be asked to enter responses to security questions and choose a password. Other methods of password setup may also be understood and may be implemented as may be desired.

A pharmacy client admin may, in some exemplary embodiments, be able to add pharmacy locations, edit/deactivate pharmacy locations, add users for each pharmacy (for example, by providing a name, contact details, and an email ID), add notification contact details (such as, for example, email ID or mobile number) for each pharmacy, and perform any other management actions.

According to an exemplary embodiment, users that have been authorized by a pharmacy client admin may be able to login with their credentials and send/receive prescription transfers through the portal. According to an exemplary embodiment, pharmacies, which may include pharmacy client admins and authorized users, may be able to generate reports for their list of transactions, revenue generated, and any further information (which may again be filterable).

In an exemplary embodiment, each transaction may be charged, to one or both of a transferring and a receiving pharmacy. (In an exemplary embodiment, payment may happen instantaneously, or may happen at a designated time, such as on the last day of the month. For example, a scheduler may be run at the end of the month to determine the amount to be deducted from each pharmacy payment account). In an exemplary embodiment, a receiving pharmacy may only be charged if they respond to the transfer request.

In an exemplary embodiment, a set of pharmacy modules 204 may include a sending pharmacy module 206 and a receiving pharmacy module 208, which may each be available to each pharmacy, and may operate depending on whether the pharmacy is operating in a sending or receiving capacity.

Looking first at the transferring pharmacy module 206, according to an exemplary embodiment, a pharmacy user may be able to create a patient record, which may require entering patient details like name, address, gender, DOB, insurance information, etc. In an exemplary embodiment, the transferring pharmacy module 206 may allow a pharmacy user to view a list of patients, and may allow them to perform a patient management function by which they can update patient information.

According to an exemplary embodiment, a pharmacy user may be able to send prescriptions in the "send prescription" screen, for each patient for which a record has been created. A "send prescription" screen may include, for example, patient details (such as those already added), a name of the drug to be sent (which may, in an exemplary embodiment, be subject to a drug name check by which the name of the drug to be sent may be validated against an integrated drug database), a dose, a drug strength, instructions, frequency, duration, a prescribing physician, a "refill allowed" flag, and information about the receiving pharmacy. According to an exemplary embodiment, a "send prescription" screen may be populated with a list of registered pharmacies, which may allow a pharmacy user to easily select a destination pharmacy.

According to an exemplary embodiment, once all fields are filled, a sending pharmacy user may be able to send out the prescription to the receiving pharmacy through the "send prescription" screen of the transferring pharmacy module 206. In an exemplary embodiment, this may update the status of the prescription in the pharmaceutical prescription transfer system 200 to be "sent." (According to an exemplary embodiment, a sending pharmacy user may also be able to send the prescription through e-fax, or external fax or another method, in addition to sending the prescription within the application. In such embodiments, it may be desirable to verify that a prescription has been sent only when it is received, if desired.)

According to an exemplary embodiment, a transferring pharmacy may be able to search for patients (such as, for example, patients on a list of patients added by that pharmacy), prescriptions (including prescriptions sent/received by that pharmacy), patient statuses and prescription statuses, along with any other information such as may be desired. According to an exemplary embodiment, a transferring pharmacy may continue to receive notifications pertaining to transferred prescriptions, if desired; for example, a transferring pharmacy may receive a notification when the status of a prescription has been changed.

Looking next at the receiving pharmacy module 208, a receiving pharmacy module 208 may be configured to provide receiving pharmacy users notifications or reminders when a new prescription has been received. In an exemplary embodiment, these notifications or reminders may be provided in the pharmaceutical prescription transfer system 200; in another exemplary embodiment, these notifications or reminders may be provided via another communication method (such as, for example, email, telephone, SMS or MMS text messaging, or any other communication method, which may be customized by the user if desired). According to an exemplary embodiment, a receiving pharmacy module 208 may further be configured to receive e-faxes, if such an option was selected or utilized by the transferring pharmacy.

In an exemplary embodiment, once a communication is received from the transferring pharmacy, the receiving pharmacy module 208 may automatically update the status of the prescription transfer request to "received," or may allow a user to do so, in order to acknowledge the receipt of the prescription and the presence of all essential details. If the receiving pharmacy module 208 does not update the status of the prescription transfer request to "received" within a given period of time, the pharmaceutical prescription transfer system 200 may provide another notification to the receiving pharmacy module 208, optionally through another communications medium (for example, if the first notification is provided in-portal, the second notification may be provided via email or SMS, as may be desired). Once the transferred medicines are dispensed, the status of the prescription transfer may be changed to "dispensed" in the receiving pharmacy module. This may send another notification to the transferring pharmacy.

In an exemplary embodiment, a pharmaceutical prescription transfer system 200 may be integrated with a pharmacy management application 218. According to such an exemplary embodiment, the pharmaceutical prescription transfer system 200 may be configured to automatically update the pharmacy management application 218 and vice-versa; for example, when a prescription is marked as being dispensed in the pharmacy management application 218, it may likewise be marked as being dispensed by the receiving pharmacy module 208. Exemplary pharmacy management applications 218 may include, for example, PIONEERRX, WINRX, PRIMECARE, or other such system as may be desired.

Figure 3:
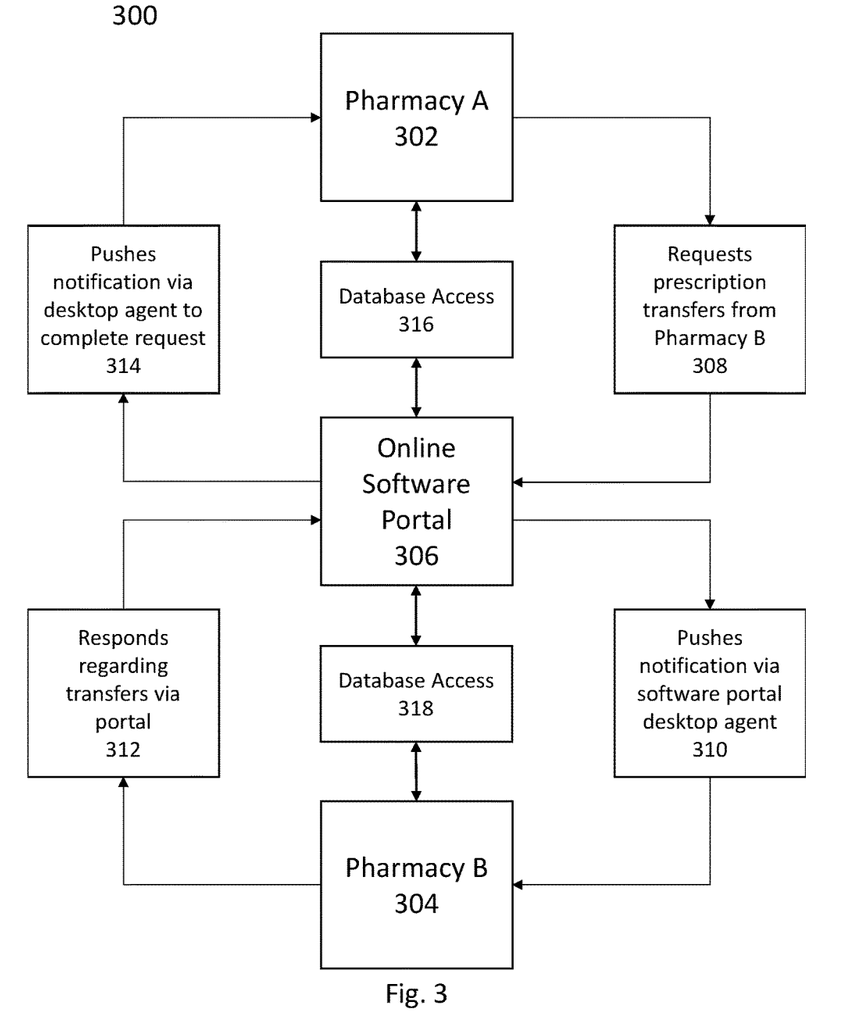
FIG. 3 is an exemplary embodiment of a process for using a pharmaceutical prescription transfer system incorporating aspects of the system architecture.

Turning now to exemplary FIG. 3, FIG. 3 displays an exemplary embodiment of a process for using a pharmaceutical prescription transfer system 300, which in this case incorporates aspects of the system architecture. According to an exemplary embodiment, a first pharmacy, Pharmacy A 302, may request a prescription transfer from a second pharmacy, Pharmacy B 304, via a web portal 306. In an exemplary embodiment, this may be done by a transfer request 308 directed toward the web portal 306.

In a next step 310, the web portal 308 may provide a notification 310 to Pharmacy B 304, for example via a software portal desktop agent operating on a computer system of Pharmacy B 304. Pharmacy B 304 may then respond regarding the transfers 312 via the portal 306. The online software portal 306 may then provide a notification 314 to Pharmacy A 302, for example via a software portal desktop agent operating on a computer system of Pharmacy A 302. Pharmacy A 302 may then finish updating its records based on the received notification 314, and may receive any other notifications that may be applicable (such as separate "received" and "dispensed" notifications provided by the online software portal 306), such as may be desired.

According to an exemplary embodiment, the online software portal 306 may be integrated with centralized database software, independent of any database software or pharmacy management applications of the individual pharmacies, such as Pharmacy A 302 or Pharmacy B 304. In some exemplary embodiments, access to this database software 316, 318 may thus be shared between the online software portal 306 and the software portal desktop agents available to Pharmacy A 302 and Pharmacy B 304. In some exemplary embodiments, the software portal 306 may instead be integrated with the database software of one or both of Pharmacy A 302 or Pharmacy B 304, or may be integrated with both. In another exemplary embodiment, the online software portal 306 may be utilized in an internal transfer system within a chain of pharmacies rather than a transfer system between a first pharmacy or pharmacy chain (such as Pharmacy A) and a second pharmacy or pharmacy chain (such as Pharmacy B). In such exemplary embodiments, wherein the online software portal 306 is part of an internal transfer system, there may be no distinction between the database software of Pharmacy A 302, Pharmacy B 304, and the online software portal 306. In still other exemplary embodiments, the online software portal 306 may be part of the same service (such as a cloud service) as one or more databases; for example, the pharmacies may subscribe to a database service as well as a pharmaceutical prescription transfer system which are each offered by the same company.

In some exemplary embodiments, the pharmaceutical prescription transfer system may be integrated with, via the online software portal 306 or otherwise, a pharmacy database, a drug name database, an online merchant account and/or other payment system, a prescription direction database, an option for handling multiple prescriptions at once, a detailed transaction report system, a real-time notification system that may be managed via a desktop agent, or any other features or combination of features such as may be desired. As previously described, in some exemplary embodiments, such systems may be made available via the online software portal 306, as, for example, cloud databases accessible 316, 318 by the online software portal 306 and/or Pharmacy A 302 and/or Pharmacy B 304, as may be desired.

For example, in some exemplary embodiments, a pharmacy system (such as a system of Pharmacy A 302 or a system of Pharmacy B 304) may be equipped with a system for transferring multiple prescriptions at once. In an exemplary embodiment, this may be restricted to multiple related prescriptions (such as, for example, multiple prescriptions belonging to the same person or same family) or may be configured to allow transferring of multiple unrelated transfers (such as, for example, if batch transfers to particular pharmacies are desired for logistical reasons). Other databases and other information may be provided and may be accessible as may be desired.

Figure 4:
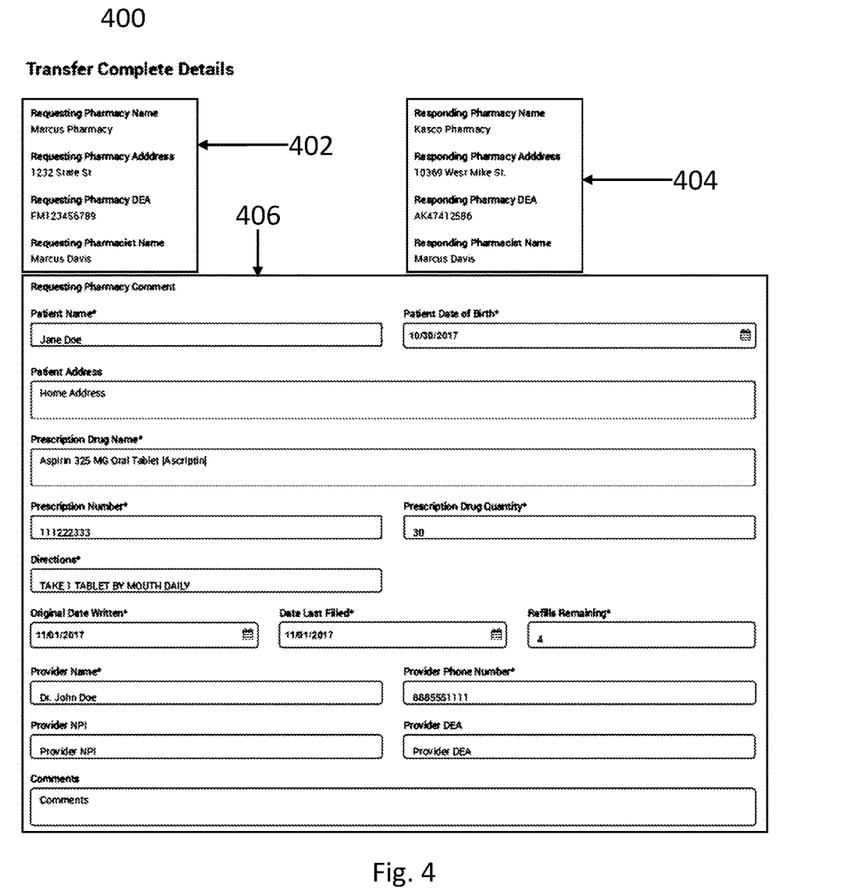
FIG. 4 is an exemplary embodiment of a completed prescription transfer file.

Turning now to exemplary FIG. 4, FIG. 4 shows an exemplary embodiment of a completed prescription transfer file 400 that may be generated by a pharmaceutical prescription transfer system or which may be output by a pharmacy system after a transfer process is performed by a pharmaceutical prescription transfer system. According to an exemplary embodiment, such a completed transfer file 400 may be automatically output by the pharmaceutical prescription transfer system after the completion of a transfer, may be automatically output by the pharmacy system after the completion of a transfer, or may be downloaded by an end user at some stage in the transfer process, such as after the completion of a transfer or after the completion of a block of transfers. As part of an output process, or after being output to a pharmacy system or other system or downloaded by an end user, the completed transfer file 400 may be printed, which may in come exemplary embodiments be performed automatically or may be done manually, as may be desired.

According to an exemplary embodiment, a completed transfer file 400 may include, for example, a set of details about the requesting pharmacy 402, such as, for example, the name of the requesting pharmacy (for example, "Marcus Pharmacy"), the street address of the requesting pharmacy (for example, "1232 State Street"), the Drug Enforcement Administration (DEA) registration number of the requesting pharmacy (for example, "FM123456789"), and the name of a requesting pharmacist (for example, "Marcus Davis"). Likewise, according to an exemplary embodiment, a completed transfer file may include, for example, a set of details about the responding or transferring pharmacy 404, such as, for example, the name of the responding pharmacy (for example, "Kasco Pharmacy"), the street address of the responding pharmacy (for example, "10369 West Mike Street"), the DEA number of the responding pharmacy (for example, "AK47412586"), and the name of a responding pharmacist (for example, "Marcus Davis").

(It may be noted that in this particular instance, the responding pharmacist is the same pharmacist as the requesting pharmacist, indicating that the pharmacist is in the process of leaving his old place of employment and moving to a new place of employment. The transfer request may in this case be motivated accordingly; for example, it may be that "Kasco Pharmacy" is shutting down entirely, with prescription transfers being made by default to the new location at which the responding pharmacist, Marcus Davis, will be practicing. In some exemplary embodiments, it may be desirable to use a pharmaceutical prescription transfer system to handle such cases where a transfer may be initiated for reasons other than a customer request, or to handle similar cases that may require records to be updated, such as a case in which a first pharmacy operating at a location is purchased by a second pharmacy and rebranded at the same location. This may ensure the consistency of records.)

According to an exemplary embodiment, a completed transfer file 400 may also include comments from one or more of the pharmacies, such as a requesting pharmacy 406, a responding or transferring pharmacy, or other pharmacies in the chain, such as a previous pharmacy from which the prescription had been transferred. (In some exemplary embodiments, the information of all transferring pharmacies, or the information of one or more transferring pharmacies before the responding pharmacy, may be shown next to the responding pharmacy information 404 or elsewhere, as may be desired.)

In an exemplary embodiment, comment information 406 may include, for example, the name of the requesting patient, the date of birth of the requesting patient, the address of the requesting patient, the prescription drug name that the patient will be receiving, the prescription number of the requesting patient (which may be, for example, an internal record number), a prescription drug quantity, prescription instructions, a date when the original prescription was written, a date the prescription was last filled, a number of refills remaining on the prescription, a prescribing physician name or other provider name, a provider phone number, a provider NPI number, a provider DEA registration number, and any other comments such as may be desired. In some exemplary embodiments, comments may be provided by other pharmacies other than the receiving pharmacy, such as the responding pharmacy or other past pharmacies, and these comments may be displayed together or may be reconciled with one another if desired. For example, in an exemplary embodiment, if the responding pharmacy has certain patient information (such as the patient's name and date of birth) and the receiving pharmacy has matching information, this may be indicated as part of preparing the completed transfer file 400. If the responding pharmacy has certain patient information and the receiving pharmacy has mismatched information (such as if a patient's name does not correctly match between the receiving and responding pharmacy records) this may be flagged as a part of preparing the completed transfer file 400, which may indicate that a transfer should be restricted or should otherwise come under greater scrutiny until the discrepancy is resolved. (For example, if the patient is requested to provide their name—or other information, such as the name of an originally prescribing physician—to request the transfer, the patient's name may have changed due to marriage and may be different. This discrepancy may be flagged as part of the transfer process as a part of preparing the completed transfer file 400, and may be resolved by the action of one or both pharmacies, such as may be desired.)

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art (for example, features associated with certain configurations of the invention may instead be associated with any other configurations of the invention, as desired).

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A pharmaceutical prescription transfer system, comprising:
   a transferring pharmacy module; and
   a receiving pharmacy module,
   wherein each of the transferring pharmacy module and the receiving pharmacy module comprises a processor, a memory, and a network connection,
   wherein the transferring pharmacy module is configured to perform the steps of:
      accessing, with the processor, from a list of patients, a patient record, and retrieving patient information from the patient record;
      populating, with the processor, a transfer request form with the patient information;
      sending, to the receiving pharmacy module, the transfer request form comprising a transferred prescription and a transfer request notification;
      automatically printing a physical transfer document, and sending, via the network connection, a notification that the physical transfer document was sent via an external device;
      maintaining a transferred prescription status record for the transferred prescription;
      receiving, via the network connection, a receipt notification from the receiving pharmacy module; and
      providing the receipt notification to a transferring module user, and
   wherein the receiving pharmacy module is configured to perform the steps of:
      receiving, via a network connection, the transfer request notification from the transferring pharmacy module, the transfer request notification comprising the patient information;
      providing the transfer notification to a receiving module user;
      updating the transferred prescription status record to a received status and providing the receipt notification to the transferring pharmacy module;

authorizing dispensation of the transferred prescription; and automatically generating a completed transfer record.

2. The system of claim 1, wherein the step of providing the receipt notification to the transferring module user comprises providing an in-portal notification to the transferring module user, and further comprises sending an external notification from the transferring pharmacy module to an external device of the transferring module user by at least one of email or SMS.

3. The system of claim 1, wherein the step of providing the transfer notification to the receiving module user comprises providing an in-portal notification to the receiving module user, and further comprises sending an external notification from the receiving pharmacy module to an external device of the receiving module user by at least one of email or SMS.

4. The system of claim 3, wherein the system is further configured to perform the steps of:

determining whether the transferred prescription status record of the transferred prescription has been updated to the received status; and sending an additional external notification to the external device of the receiving module user after a predetermined amount of time has passed and after the transferred prescription status record of the transferred prescription has not been updated to the received status.

5. The system of claim 1, further comprising updating, on the receiving pharmacy module, the transferred prescription status record to a dispensed status and providing a dispensation notification to the transferring pharmacy module.

6. The system of claim 1, wherein the step of sending, to the receiving pharmacy module, the transfer request form comprises accessing an integrated electronic fax program and sending the transfer request form via the integrated electronic fax program.

7. The system of claim 1, wherein the system is further configured to perform the steps of submitting, from the transferring pharmacy module, to a super administrator portal, a transfer record;

submitting, from the receiving pharmacy module, to a super administrator portal, at least one of a receipt record or a nonresponse record;

deducting a payment from a payment account associated with the transferring pharmacy module;

when a receipt record is submitted, deducting a payment from a payment account associated with the receiving pharmacy module; and when a nonresponse record is submitted, deducting no payment from a payment account associated with the receiving pharmacy module.

8. The system of claim 1, wherein the step of populating, with the processor, a transfer request form with the patient information comprises accessing an integrated drug database and performing a drug validity check via the integrated drug database.

9. The system of claim 1, wherein the system further comprises a pharmacy management application, and wherein the pharmacy management application automatically updates the transferred prescription status record in the receiving pharmacy module when the transferred prescription is dispensed.

10. A method of providing pharmaceutical transfers using a pharmaceutical prescription transfer system comprising a transferring pharmacy module and a receiving pharmacy module, each of the transferring pharmacy module and the receiving pharmacy module comprising a processor, a memory, and a network connection, the method comprising:

accessing, with the processor of the transferring pharmacy module, from a list of patients, a patient record, and retrieving patient information from the patient record;

populating, with the processor of the transferring pharmacy module, a transfer request form with the patient information;

sending, to the receiving pharmacy module, the transfer request form comprising a transferred prescription and a transfer request notification;

automatically printing a physical transfer document, and sending, via the network connection, a notification that the physical transfer document was sent via an external device;

maintaining a transferred prescription status record for the transferred prescription;

receiving, via the network connection of the transferring pharmacy module, a receipt notification from the receiving pharmacy module;

providing the receipt notification to a transferring module user;

receiving, via a network connection of the receiving pharmacy module, the transfer request notification from the transferring pharmacy module, the transfer request notification comprising the patient information;

providing the transfer notification to a receiving module user;

updating the transferred prescription status record to a received status and providing the receipt notification to the transferring pharmacy module;

dispensing the transferred prescription; and automatically generating a completed transfer record.

11. The method of claim 10, wherein the step of providing the receipt notification to the transferring module user comprises providing an in-portal notification to the transferring module user, and further comprises sending an external notification from the transferring pharmacy module to an external device of the transferring module user by at least one of email or SMS.

12. The method of claim 10, wherein the step of providing the transfer notification to the receiving module user comprises providing an in-portal notification to the receiving module user, and further comprises sending an external notification from the receiving pharmacy module to an external device of the receiving module user by at least one of email or SMS.

13. The method of claim 12, further comprising the steps of:

determining whether the transferred prescription status record of the transferred prescription has been updated to the received status; and sending an additional external notification to the external device of the receiving module user after a predetermined amount of time has passed and after the transferred prescription status record of the transferred prescription has not been updated to the received status.

14. The method of claim 10, further comprising updating, on the receiving pharmacy module, the transferred prescription status record to a dispensed status and providing a dispensation notification to the transferring pharmacy module.

15. The method of claim 10, wherein the step of sending, to the receiving pharmacy module, the transfer request form comprises accessing an integrated electronic fax program and sending the transfer request form via the integrated electronic fax program.

16. The method of claim 10, further comprising the steps of
- submitting, from the transferring pharmacy module, to a super administrator portal, a transfer record;
- submitting, from the receiving pharmacy module, to a super administrator portal, at least one of a receipt record or a nonresponse record;
- deducting a payment from a payment account associated with the transferring pharmacy module;
- when a receipt record is submitted, deducting a payment from a payment account associated with the receiving pharmacy module; and
- when a nonresponse record is submitted, deducting no payment from a payment account associated with the receiving pharmacy module.

17. The method of claim 10, wherein the step of populating, with the processor of the transferring pharmacy module, a transfer request form with the patient information comprises accessing an integrated drug database and performing a drug validity check via the integrated drug database.

18. The method of claim 10, wherein a pharmacy management application automatically updates the transferred prescription status record in the receiving pharmacy module when the transferred prescription is dispensed.

* * * * *